(12) United States Patent
Omatsu et al.

(10) Patent No.: US 6,659,036 B2
(45) Date of Patent: Dec. 9, 2003

(54) PLASMA STERILIZATION INDICATOR

(75) Inventors: Takeshi Omatsu, Kyotanabe (JP); Satoshi Maruyama, Yao (JP)

(73) Assignee: Sakura Color Products Corporation, Osaka-Fu (JP)

( * ) Notice: Subject to any disclaimer, the term of this patent is extended or adjusted under 35 U.S.C. 154(b) by 0 days.

(21) Appl. No.: 09/738,705

(22) Filed: Dec. 15, 2000

(65) Prior Publication Data

US 2001/0054374 A1 Dec. 27, 2001

(30) Foreign Application Priority Data

Dec. 15, 1999 (JP) .......................................... 11-356320

(51) Int. Cl.$^7$ ............................................. G01D 21/00
(52) U.S. Cl. ........................ 116/206; 116/219; 422/50; 422/119; 422/22; 436/169
(58) Field of Search ................................. 116/206, 207, 116/216, 217, 219; 422/50, 119, 906, 22, 28, 32; 436/164, 166, 167, 169; 252/408.1

(56) References Cited

U.S. PATENT DOCUMENTS

| | | | | |
|---|---|---|---|---|
| 4,038,873 A | * | 8/1977 | Kimmel | ...................... 116/206 |
| 4,463,162 A | * | 7/1984 | Nogami et al. | .............. 528/190 |
| 4,991,074 A | * | 2/1991 | Kobaashi et al. | ............ 116/216 |
| 5,094,545 A | * | 3/1992 | Larsson et al. | .............. 116/217 |
| 6,117,685 A | * | 9/2000 | Omatsu et al. | .............. 436/135 |
| 6,214,623 B1 | * | 4/2001 | Simons et al. | ............... 116/207 |
| 6,267,242 B1 | * | 7/2001 | Nagata et al. | ................. 422/28 |
| 6,410,338 B1 | * | 6/2002 | Lippold et al. | .............. 436/166 |

FOREIGN PATENT DOCUMENTS

| | | | | |
|---|---|---|---|---|
| JP | 62291564 A | * | 12/1987 | .................. 116/206 |
| JP | 411140360 A | * | 5/1999 | .................. 436/135 |

* cited by examiner

Primary Examiner—Christopher W. Fulton
Assistant Examiner—Travis Reis
(74) Attorney, Agent, or Firm—Rader Fishman & Grauer

(57) ABSTRACT

There is provided a plasma sterilization indicator enabling an accurate detection of the end-point of plasma sterilization. This invention relates to a plasma sterilization indicator comprising a support and, as formed thereon, a color-change layer comprised of a variable color ink composition containing an anthraquinone dye having at least one kind of amino groups, primary and/or secondary.

5 Claims, 2 Drawing Sheets

PLASMA STERILIZATION INDICATOR

FIELD OF THE INVENTION

This invention relates to a plasma sterilization indicator.

BACKGROUND OF THE INVENTION

The various equipment and ware used in hospitals, laboratories, etc. are sterilized for disinfection. As techniques of such sterilization, steam sterilization, ethylene oxide gas sterilization and plasma sterilization, among others, are known. Among these techniques, the plasma sterilization technique comprises sterilizing a sterilizing load by means of a low-temperature plasma generated in an oxidizing gas atmosphere such as vaporized hydrogen peroxide and, as such, has the advantage that the required sterility can be attained at a comparatively low temperature.

The plasma sterilization technique, just as the other techniques, requires the provision of an indicator for verifying the sterility of a lot. Thus, an indicator for detecting the sterilizing gas concentration and exposure time must be provided in the plasma sterilization system.

As the prior art relevant to such an indicator, there is known a system for monitoring a course of low-temperature gas plasma sterilization involving an atmosphere composed predominantly of peracetic acid and acetic acid, for instance, wherein an indicator utilizing bromophenol blue, a pH indicator, is used to detect the sterility of a lot by taking advantage of the change in color from brilliant blue to light yellow owing to the activity of peracetic acid or acetic acid (U.S. Pat. No. 5,482,684).

However, the above indicator tends to reassume the initial color (the color before color change) if left standing for some time after the color change indicative of sterility and, therefore, has a drawback in terms of the steadiness of indication after color change. Once the indicator has reassumed the initial color, there is no telling any longer whether the sterilizing load in the system has successfully gone through sterilization.

SUMMARY OF THE INVENTION

It is, therefore, a primary object of the invention to provide a plasma sterilization indicator with which the end-point of plasma sterilization can be more accurately ascertained. The inventor of this invention did much research to overcome the foregoing drawback of the prior art and found that the above object can be accomplished by using a herein-defined ink composition in a plasma sterilization atmosphere. This invention is grounded on the above finding.

This invention, therefore, relates to the following plasma sterilization indicators.

1. A plasma sterilization indicator comprising a support and, as formed thereon, a color-change layer comprised of a variable color ink composition containing an anthraquinone dye having at least one amino group selected from the group consisting of a primary amino group and a secondary amino group.
2. The plasma sterilization indicator set forth in the above paragraph 1 which further comprises a non-color-change layer which does not change color in a plasma sterilization atmosphere as formed on said support and/or on said color-change layer.
3. The plasma sterilization indicator set forth in the above paragraph 1 wherein the variable color ink composition further contains a cationic surfactant of the quaternary ammonium salt type.
4. The plasma sterilization indicator set forth in the above paragraph 3 wherein the cationic surfactant of the quaternary ammonium salt type is an alkyl trimethylammonium salt.
5. The plasma sterilization indicator set forth in the above paragraph 1 which further comprises an extender and/or a resinous binder.
6. A method of detecting the sterility of a plasma-sterilizing load which comprises disposing the indicator defined in the above paragraph 1 in a plasma sterilization atmosphere and checking to see a change in color of said color-change layer.

DETAILED DESCRIPTION OF THE INVENTION

Figure 1:
FIG. 1 is a view showing the design printed with a variable color ink composition in Example 3.

The plasma sterilization indicator of the invention comprises a color-change layer comprised of a variable color ink composition containing an anthraquinone dye having at least one kind of amino group, namely primary and/or secondary, as disposed on a support.

The variable color ink composition contains an anthraquinone dye having at least one amino group selected from the group consisting of a primary amino group and a secondary amino group.

The anthraquinone dye is not particularly restricted insofar as it has an anthraquinone structure as the nucleus and at least one kind of amino group, primary and/or secondary, and various known disperse dyes in the anthraquinone series can likewise be utilized. Each kind of amino group in the dye molecule may number more than one and such amino groups may be of the same species or different species.

More particularly, there can be mentioned 1,4-diaminoanthraquinone (C.I. Disperse Violet 1), 1-amino-4-hydroxy-2-methoxyanthraquinone (C.I. Disperse Red 4), 1-amino-4-methylaminoanthraquinone (C.I. Disperse Violet 4), 1,4-diamino-2-methoxyanthraquinone (C.I. Disperse Red 11), 1-amino-2-methylanthraquinone (C.I. Disperse Orange 11), 1-amino-4-hydroxyanthraquinone (C.I. Disperse Red 15), 1,4,5,8-tetraaminoanthraquinone (C.I. Disperse Blue 1), and 1,4-diamino-5-nitroanthraquinone (C.I. Disperse Violet 8), among others [Dye Nos.(i.e. C.I. Generic Names) in parentheses]. In addition, dyes generally known as C.I. Solvent Blue 14, C.I. Solvent Blue 63, C.I. Solvent Violet 13, C.I. Solvent Violet 14, C.I. Solvent Red 52, C.I. Solvent Red 114, C.I. vat Blue 21, C.I. Vat Blue 30, C.I. Vat Violet 15, C.I. Vat Violet 17, C.I. Vat Red 19, C.I. Vat Red 28, C.I. Acid Blue 23, C.I. Acid Blue 80, C.I. Acid Violet 43, C.I. Acid Violet 48, C.I. Acid Red 81, C.I. Acid Red 83, C.I. Reactive Blue 4, C.I. Reactive Blue 19, C.I. Disperse Blue 7, etc. can also be employed. These anthraquinone dyes can be used each independently or in a combination of 2 or more species. The preferred, among these anthraquinone dyes, are C.I. Disperse Blue 7 and C.I. Disperse Violet 1, for instance. Furthermore, in the present invention, the sensitivity of detection can be controlled by varying the species (e.g. molecular structures) of such anthraquinone dyes to be used.

In the practice of the invention, dyes other than said anthraquinone dyes as well as pigments may also be used concomitantly. Particularly, a coloring material which does not change color in the plasma sterilization atmosphere ("non-color-change color") may be incorporated. By so doing, the level of visual recognition of a change in color from one tone to another can be enhanced. As said non-color-change color, the known ink (regular color ink) can be used. The level of use of such a non-color-change color can be judiciously selected according to the kind of non-color-change color, among other variables.

In the present invention, it is more preferable that the variable color ink composition containing said anthraquinone dye further contain a cationic surfactant of the quaternary ammonium salt type.

This cationic surfactant of the quaternary ammonium salt type (hereinafter referred to briefly as "cationic surfactant" at times) is not particularly restricted but usually alkylammonium salts, which may be commercial products, can be employed. Furthermore, these may be used each independently or in a combination of 2 or more species. In the present invention, a still higher detection sensitivity can be obtained by using such a cationic surfactant in combination with said anthraquinone dye.

The preferred, among such cationic surfactants, are alkyltrimethylammonium salts and dialkyldimethylammonium salts. To cite specific examples, cocoalkyltrimethylammonium chloride, tallowalkyltrimethylammonium chloride, behenyltrimethylammonium chloride, hexadecyltrimethylammonium chloride, lauryltrimethylammonium chloride, octadecyltrimethylammonium chloride, dioctyldimethylammonium chloride, distearyldimethylammonium chloride and alkylbenzyldimethylammonium chloride can be mentioned. Particularly preferred are cocoalkyltrimethylammonium chloride and lauryltrimethylammonium chloride.

The variable color ink composition may contain various other components which are used in the known inks, such as a resinous binder, an extender and a solvent, in suitable amounts.

The resinous binder can be judiciously selected according to the kind of support used and the known resin components used in writing or printing ink compositions can be used as they are. Specifically, maleic acid resins, amide resins, ketone resins, alkylphenol resins, rosin-modified resins, polyvinyl butyral, polyvinylpyrrolidone, and cellulosic resins can be mentioned by way of example.

The extender is not particularly restricted but includes bentonite, activated clay, alumina, silica gel and so on. Aside from these, those materials which are generally known as body pigments or extender pigments can also be mentioned. Among these, porous extenders, particularly silica gel, are preferred. By adding such an extender, chiefly the sensitivity of detection can be improved.

The solvent which can be used in the practice of the invention includes all the solvents that are generally used in printing or writing ink compositions. For example, various solvents in the alcohol, ester, ether, ketone and hydrocarbon series are usable, and a choice can be judiciously made according to the solubility of the dye and resinous binder used, among other variables.

The formulating amounts of those components can be judiciously selected according to the kind of each component used and the intended application. By way of illustration, when the anthraquinone dye is to be used in combination with said resinous binder and extender, the usual formulation may be 0.05~5 weight % (preferably 0.1~1 weight %) of the anthraquinone dye, not more than 50 weight % (preferably 5~35 weight %) of the resinous binder, and 1~30 weight % (preferably 2~20 weight %) of the extender, with the balance being comprised of a solvent and/or the like.

When the cationic surfactant mentioned above is to be further added, the formulating amounts of the various components of a variable color ink composition may be 0.05~10 weight % (preferably 0.1~1 weight %), of the anthraquinone dye, 0.2~30 weight % (preferably 0.5~10 weight %) of the cationic surfactant, not more than 50 weight % (preferably 5~35 weight %) of the resinous binder and 1~30 weight % (preferably 2~20 weight %) of the extender, with the balance being comprised of the solvent and/or the like.

These components can be added all at once or serially and mixed uniformly in a known mixer such as a homogenizer, a dissolver or the like. An exemplary procedure comprises adding the anthraquinone dye to the solvent in the first place and then adding the cationic surfactant where needed, as well as the resinous binder, extender, etc. and mixing them uniformly in a mixer.

The support of the indicator according to the invention is not particularly restricted insofar as a color-change layer can be constructed thereon. Thus, for example, supports made of metals, metal alloys, wood, paper, ceramics, glass, concrete, plastics, fibrous materials (nonwoven or woven fabrics and other sheets), and composites thereof can be employed.

The color-change layer according to the invention may be a layer which changes color from one tone to another or a layer which undergoes fading or lose color.

The color-change layer can be constructed using the variable color ink composition of the invention by various known techniques such as silk screen printing, gravure printing, offset printing, relief printing, flexographic printing and so on. Methods other than printing may also be utilized. For example, the color-change layer can be formed by dipping the support in the variable color ink composition. This method is particularly suited to ink-permeable support materials such as paper and nonwoven cloth.

In accordance with the invention, a non-color-change layer which does not change color in the plasma sterilization atmosphere may be further constructed on said support and/or on said color-change layer. The non-color-change layer can be formed with a commercial regular color ink. For example, this layer can be formed using a water-based ink, an oil-based ink or a non-solvent ink. The ink to be used for the formation of such a non-color-change layer may contain the components of the known ink, such as the resinous binder, extender and solvent.

Formation of the non-color-change layer can be carried out in the same manner as formation of said color-change layer. For example, the non-color-change layer can be formed using a regular color ink by any known printing technique such as silk screen printing, gravure printing, offset printing, relief printing or flexographic printing. The printing order for the formation of the color-change layer and non-color-change layer is not particularly restricted but can be judiciously selected according to the design to be printed, for instance.

The indicator of the invention may comprise said color-change layer and non-color-change layer each as a single layer or as a plurality of layers. Moreover, such a plurality of color-change layers or non-color-change layers may be formed adjacent to each other. In such cases, the color-change layers may be of the same composition or different compositions. Similarly, the non-color-change layers may be of the same composition or different compositions.

Furthermore, the color-change layer and non-color-change layer may be formed all over the surface of a support or another layer or only in a limited area of the surface. In such cases, particularly to insure a positive change in color of the color-change layer, the color-change layer and non-color-change layer can be formed in such a manner that part or the whole of the color-change layer on at least one level will be exposed to the plasma sterilization atmosphere.

In the present invention, the color-change layer and non-color change layer can be provided in any desired combination inasmuch as the end-point of plasma sterilization can be indicated. For example, the color-change layer and non-color-change layer may be so designed that the color difference between the two layers becomes apparent only after change in color of the color-change layer or the color difference between the color-change layer and the non-color-change layer disappears upon change in color of the color-change layer. In the invention, the color-change layer and the non-color-change layer are preferably formed in such a manner that the color difference between the two layers will become apparent only after the change in color of the color-change layer.

To insure a positive recognition of a color difference, the color-change layer and the non-color-change layer may for example be so constituted that at least a member of the group consisting of character, figure and symbol designs will appear upon change in color of the color-change layer. In the context of this invention, said character, figure and symbol designs mean any and all information that will more specifically alert an observer to a change in color. Such character and other designs can be judiciously selected according to the intended application.

The color-change layer prior to color change and the non-color-change layer may be constituted in dissimilar colors. For example, the two layers may be formed in substantially the same color but in such a manner that only after color change of the color change layer does the color difference (contrast) between the color-change layer and the non-color-change layer become conspicuous.

In the indicator of the invention, the color change layer and the non-color-change layer can be formed avoiding an overlap therebetween. By so doing, savings can be obtained in the quantity of inks required.

Furthermore, in the present invention, another color-change layer or a non-color-change layer may be formed on at least one of the color-change layer and non-color-change layer. For example, on the stratum comprised of the color-change layer and non-color-change layer formed in a mutually excluding fashion, namely without overlap ("color-change/non-color-change stratum"), a color-change layer having a different design can be formed and, in such cases, the boundary between the color-change layer and the non-color-change layer can be made substantially indiscernible, thus contributing to an improved design quality.

The indicator of the invention can be applied to any plasma sterilization treatment carried out in an oxidizing gas atmosphere. It is particularly suitable for the plasma sterilization carried out in a hydrogen peroxide ($H_2O_2$) gas atmosphere. The plasma sterilization can be carried out according to the known protocol. For example, the treatment gas atmosphere is first decompressed from atmospheric pressure to 1 Torr or less (preferably 0.3~0.8 Torr) (pressure reduction step), then a high-frequency energy is applied to the atmosphere to create an air plasma for demoisturization and warming of the sterilizing load to render the load susceptible to sterilization (preconditioning step). Then, hydrogen peroxide (a ca 58% solution of hydrogen peroxide) is gasified by feeding air through a HEPA-filter and forced to diffuse into the atmosphere (hydrogen peroxide injection/gassification step). After a reduced pressure is reestablished, a high-frequency energy is applied to the atmosphere to create a low-temperature $H_2O_2$ plasma, whereupon microorganisms are destroyed by the active species free radicals (low-temperature plasma step). As the supply of the high-frequency energy is stopped, the plasma comes to an end instantly and the stable $O_2$ and $H_2O$ remain. After the above hydrogen peroxide injection/gassification step and low-temperature plasma step are repeated twice or so, clean air is fed through the HEPA-filter and the atmospheric pressure is reinstated to complete a sterilization cycle (air substitution step). The time required for the above treatment depends on the kind and quantity of the sterilizing load, among other variables, but may usually be about 30~120 minutes.

The above sterilization treatment can be carried out using a known or commercial plasma sterilizer (more specifically, an equipment which generates a plasma in a hydrogen peroxide or other oxidizing gas atmosphere to sterilize a load).

Figure 6:
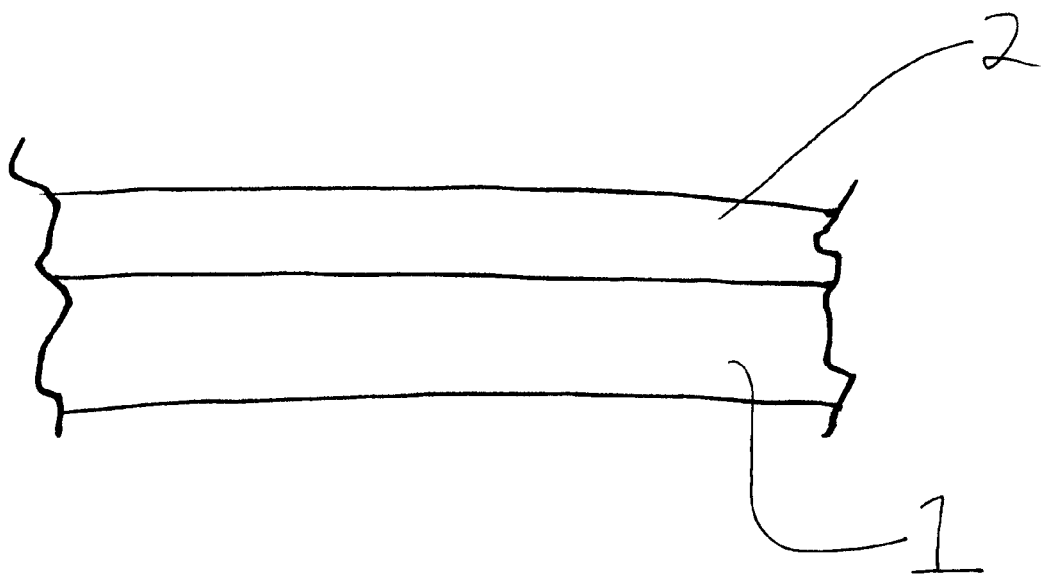
FIG. 6 is a partial side view of an example of a plasma sterilization indicator of the present invention.

An example of an indicator comprising a color-change layer may be similar to that shown in FIG. 6. The indicator comprises a substrate or support 1 that is covered with a color-change layer that comprises a variable-color ink as heretofore defined. Optionally, a non-color change layer 2 can be placed in the vicinity of the color-change layer (on support 1) to better discern a color change in the color-change layer.

Therefore, the indicator of the invention is of great use as an indicator to be used in a plasma sterilization system (more specifically, an equipment adapted to generate a plasma in a hydrogen peroxide or other oxidizing gas atmosphere to sterilize a load). For application of the indicator, all that is necessary is to dispose the indicator of the invention in a commercial plasma sterilizing equipment and let it be exposed to a plasma sterilization atmosphere alongside the ware and the like to be sterilized. Then, the sterility of the load can be verified from the color change of the indicator.

Since the indicator of the invention uses a defined anthraquinone dye for the variable color ink composition, it is highly stable without reassuming its initial color after color change, thus enabling a more positive verification of completion of plasma sterilization. Moreover, by varying the kind and formulating amount of said anthraquinone dye, the sensitivity of detection and the speed of color change can be freely controlled.

The variable color ink composition, when supplemented with a resinous binder, can be used as a printing, writing or stamping ink and put to use by coating a substrate, such as paper or film, with it.

Furthermore, the indicator of the invention enables more accurate identification of color change when a non-color-change layer is additionally provided. Moreover, with regard to the overall constitution, the indicator can be constructed in the form of a sheet or plate in which case it does not occupy any appreciable space and a flexibility feature may also be implemented by proper selection of the support, so that the indicator can be instilled in any desired location.

By using the color-change layer and non-color-change layer in a suitable combination, the indicator of the invention can be enabled to display a figure, character or symbol design appropriate to the intended application and, further, be provided with a sophisticated design, thus finding application in a broad spectrum of uses.

Particularly when a cationic surfactant of the quaternary ammonium salt type is formulated in the variable color ink composition, a more improved color-change characteristic and, hence, a higher detection sensitivity are imparted.

Furthermore, by varying the kinds and formulating amounts of said cationic surfactant, extender and other components, the detection sensitivity and the speed of color change can be liberally controlled and even quantitative determinations can be made feasible.

EXAMPLES

The following examples and comparative examples illustrate the features of the invention in further detail. It is to be understood that the invention is by no means limited to these examples.

Example 1

A mixer was charged with the following components and a variable color ink composition was prepared by mixing them together uniformly.

Anthraquinone dye ("Miketon Fast Red Violet R; product of Mitsui-Toatu Chemicals), 0.2 parts by weight
Resinous binder (the ethylcellulose resin "Ethocel 10", product of Dow Chemical), 7.35 parts by weight
Extender (the silica gel "Aerosil R-972"; product of Japan Aerosil), 9.80 parts by weight
Cationic surfactant (the coco-alkyltrimethylammonium chloride "CA2150"; product of Nikkol), 1.96 parts by weight
Solvent (the ethyl cellosolve "Seahosol MG; product of Nippon Shokubai Co., 80.69 parts by weight

Example 2

Except that 0.30 part by weight of the oil-soluble dye "VALIFAST YELLOW 4120 (product of Orient Chemical Ind.; C.I. Solvent Yellow 82) was added as non-color-change color, a variable color ink composition was prepared in otherwise the same manner as in Example 1. The level of use of the solvent was reduced by the amount corresponding to the amount of said oil-soluble dye to 80.39 parts by weight.

Test Example 1

The color-change characteristics of the variable color ink compositions obtained in Examples 1 and 2 were evaluated.

Using the respective variable color ink compositions, silk screen printing (150-mesh) was made on sheets of Kent paper. The resulting prints were set in a plasma sterilizer (STERRAD 100, Johnson and Johnson Medical; hydrogen peroxide gas used) and a sterilization treatment was performed under the standard conditions (temperature: ca 45° C., humidity: ca 10% RH). As a result, a prominent color change was observed in each case. The results are shown in Table 1. The color as so changed was persistent even after 3 months of standing, showing an excellent stability of indication.

TABLE 1

| | Beforetreatment | Aftertreatment |
|---|---|---|
| Example 1 | Violet | Violet disappeared (color of Kent paper) |
| Example 2 | Brown | Yellow |

Example 3

Using the variable color ink composition prepared in Example 1, an indicator was fabricated.

Using the above variable color ink composition, the character design "STERILIZED" (dropout) illustrated in FIG. 1 was printed on a sheet of Kent paper by the silk screen (150-mesh) printing technique to form a color-change layer. Then, avoiding overlap with the color-change layer, the character design "STERILIZED" illustrated in FIG. 2 was similarly printed by silk printing (300-mesh) with a regular color ink to form a non-color-change layer, whereby an indicator colored solid light-violet all over was obtained.

The regular color ink (light violet) mentioned above was prepared by mixing 60.6 parts by weight of the white ink "Conc 061-a", 6.1 part by weight of the violet ink "082A" and 33.3 parts by weight of the medium ink "Medium" (all in "Serikol JM Series (Matte Type)"; Teikoku Ink).

Figure 2:
FIG. 2 is a view showing the design printed with a standard color ink in Example 3.

In the practice of the invention, it is optional to allocate which of the designs illustrated in FIGS. 1 and 2 to the color-change layer or the non-color-change layer. The order of printing of the two designs is also optional.

The above indicator was set in the same plasma sterilizer as used in Test Example 1 and exposed to a sterilizing atmosphere under the standard conditions. As a result, the color-change layer alone faded so that the character design of the non-color-change layer appeared for the first time to render the letters "STERILIZED" legible in light-violet color. The color as so changed was persistent even after 3 months of standing in a room, showing a good stability of indication.

Example 4

An indicator was fabricated using the variable ink composition prepared in Example 1 and the same ordinary color ink as used in Example 3.

Figure 3:
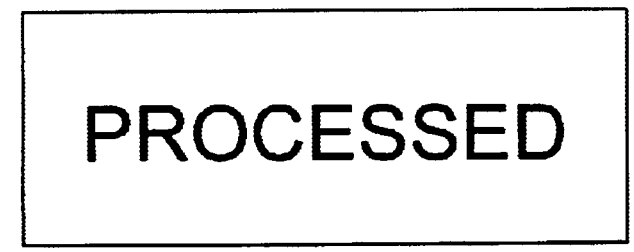
FIG. 3 is a view showing the design printed with a variable color ink composition in Example 4.
Figure 4:
FIG. 4 is a view showing the design printed with a regular color ink in Example 4.
Figure 5:
FIG. 5 is a view showing the design printed with a viable color ink composition in Example 4.

Using the above variable color ink composition, the character design "STERILIZED" illustrated in FIG. 3 was printed on a sheet of Kent paper by the silk screen (150-mesh) printing technique to form a color-change layer. Then, avoiding overlap with the color-change layer, the character design "STERILIZED" (dropout) illustrated in FIG. 4 was printed on the sheet using the regular color ink by silk screen (300-mesh) printing to form a non-color-change layer. In addition, using the above ink composition, the character design (fine English letters) illustrated in FIG. 5 was printed all over the non-color-change layer by silk screen (300-mesh) printing to form a color-change layer and provide a finished indicator. The formation of this color-change layer made the boundary between the color-change layer and non-color-change layer substantially indiscernible.

The above indicator was set in the same plasma sterilizer as used in Test Example 1 and exposed to a sterilizing atmosphere under the standard conditions. As a result, the English-letter design faded out in the first place and then the dropout color-change layer (the exposed area of the color-change layer) faded out so that ultimately the character design "STERILIZED" became legible as white letters due to the contrast against the non-color-change layer. The color as so changed was persistent even after 3 months of standing in a room, showing a good stability of indication.

Example 5

An indicator was fabricated using the variable ink composition prepared in Example 1 and a regular color ink. The regular color ink was prepared by mixing 38.8 parts by weight of the white ink "Conc 061-a", 2.6 parts by weight of the violet ink "082-A", 0.9 parts by weight of the ultramarine ink "037-b", and 57.7 parts by weight of the medium ink "Medium" (all inks are in the Serikol JM Series (Matte Type), Teikoku Ink).

Using the above variable color ink composition, a color-change layer was printed all over the surface of a sheet of Kent paper by silk screen (300-mesh) printing. Then, all over the surface of the color-change layer, the character design "STERILIZED" (dropout) illustrated in FIG. 4 was printed using the regular color ink by silk screen (300-mesh) printing to form a non-color-change layer and provide an indicator.

The above indicator was set in the same plasma sterilizer as used in Test Example 1 and exposed to a sterilizing atmosphere under the standard conditions. As a result, the dropout color-change layer (that area of the color-change layer which was directly exposed to the plasma sterilization atmosphere) faded out so that ultimately the character design "STERILIZED" became legible as white letters due to the contrast against the non-color-change layer. The color as so changed was fully sustained even after 3 months of standing in a room, showing a good stability of indication.

What is claimed is:

1. A method of detecting the sterility of a sterilizing load which comprises:

disposing a plasma sterilization indicator in a plasma sterilization atmosphere, wherein the plasma sterilization indicator comprises a support, and, as formed thereon, a color change layer comprised of a variable-color ink composition containing an anthraquinone dye having at least one amino group selected form the group consisting of a primary amino group and a secondary amino group; and checking to see a change in color of said color-change layer.

2. A method according to claim 1, wherein the indicator further comprises a non-color-change layer which does not change color in a plasma sterilization atmosphere as disposed on said support and/or on said color-change layer.

3. A method according to claim 1, wherein the variable-color ink composition further contains a cationic surfactant of the quaternary ammonium salt type.

4. A method according to claim 3, wherein the cationic surfactant of the quaternary ammonium salt type is an alkyl-trimethylammonium salt.

5. A method according to claim 1, wherein the variable-color ink composition further contains an extender and/or a resinous binder.

* * * * *